United States Patent
Eggleston et al.

(10) Patent No.: US 8,100,371 B2
(45) Date of Patent: Jan. 24, 2012

(54) I.V. SUPPORT STAND AND CLAMP APPARATUS

(75) Inventors: Gray John Eggleston, Jannali (AU); James Ross Little, Jannali (AU)

(73) Assignee: Ergotech Health Systems Pty Ltd., Turramurra (AU)

( * ) Notice: Subject to any disclaimer, the term of this patent is extended or adjusted under 35 U.S.C. 154(b) by 966 days.

(21) Appl. No.: 11/422,878

(22) Filed: Jun. 7, 2006

(65) Prior Publication Data

US 2007/0023587 A1 Feb. 1, 2007

Related U.S. Application Data

(63) Continuation-in-part of application No. PCT/AU2004/001589, filed on Nov. 18, 2004.

(30) Foreign Application Priority Data

Dec. 15, 2003 (AU) .................... 2003906942
May 17, 2004 (AU) .................... 2004902625
Jun. 8, 2005 (AU) .................... 2005902977

(51) Int. Cl.
A47F 5/00 (2006.01)

(52) U.S. Cl. .............. 248/125.8; 240/188.6; 5/601

(58) Field of Classification Search .......... 248/411, 248/410, 188.6, 171, 166, 170, 168, 125.8, 248/125.1, 188.5, 188.7, 528, 150, 151, 157, 248/165, 167, 434, 435, 155.2, 155.3; 5/601, 5/600, 658, 503.1

See application file for complete search history.

(56) References Cited

U.S. PATENT DOCUMENTS

| 774,487 | A | * | 11/1904 | Marten .............. 248/125.2 |
| 1,490,650 | A | | 4/1924 | Wagner |
| 1,844,113 | A | | 2/1932 | Beidler et al. |
| 2,598,753 | A | | 6/1952 | Bolsey |
| 2,705,119 | A | * | 3/1955 | Ingwer ............... 248/55 |

(Continued)

FOREIGN PATENT DOCUMENTS

CN 2669873 Y 1/2005

(Continued)

OTHER PUBLICATIONS

Feb. 16, 2010 Office Action in corresponding British Application GB0611219.7 (Published UK Patent Application No. GB 2428383A, published on Jan. 31, 2007).

(Continued)

*Primary Examiner* — Kimberly Wood
(74) *Attorney, Agent, or Firm* — Ostrager Chong Flaherty & Broitman P.C.

(57) ABSTRACT

An I.V. support stand (10) includes a support section and a base (20). The base (20) includes a base body and a plurality of wheel assemblies (24), each wheel assembly including a wheel support (26) operatively mounted to the base body for pivotal movement relative thereto and at least one wheel (28) operatively mounted to the wheel support. The wheel supports are pivotally movable relative to the base body between an extended position in which the wheels rest on a support surface and retracted position, the arrangement being such that when the base is disposed on the support surface the wheels are caused to adopt the extended position and when the base is moved clear of the support surface the wheel assemblies are caused to adopt the retracted position.

9 Claims, 8 Drawing Sheets

U.S. PATENT DOCUMENTS

| | | | |
|---|---|---|---|
| 2,919,094 A * | 12/1959 | Petrick | 248/171 |
| 4,183,579 A * | 1/1980 | Gonzalez y. Rojas | 297/195.11 |
| 4,245,666 A * | 1/1981 | Norris | 137/357 |
| 4,511,158 A | 4/1985 | Varga et al. | |
| 4,572,536 A | 2/1986 | Doughty | |
| 4,744,536 A | 5/1988 | Bancalari | |
| 4,886,237 A | 12/1989 | Dennis | |
| 4,892,279 A | 1/1990 | Lafferty et al. | |
| 4,932,719 A * | 6/1990 | Gonzalez y. Rojas | 297/338 |
| 5,137,236 A * | 8/1992 | Burns | 248/171 |
| 5,161,764 A | 11/1992 | Roney | |
| 5,306,109 A | 4/1994 | Kreuzer et al. | |
| 5,319,816 A | 6/1994 | Ruehl | |
| 5,355,539 A | 10/1994 | Boettger | |
| 5,366,191 A | 11/1994 | Bekanich | |
| 5,499,721 A | 3/1996 | Hansen et al. | |
| 5,699,988 A | 12/1997 | Boettger et al. | |
| 5,975,499 A * | 11/1999 | Ostrobrod | 254/332 |
| 6,016,594 A * | 1/2000 | Frey | 29/402.08 |
| D457,239 S | 5/2002 | Kunik | |
| 2005/0051682 A1 * | 3/2005 | Tuohy et al. | 248/176.1 |
| 2006/0086869 A1 * | 4/2006 | Hsieh | 248/171 |

FOREIGN PATENT DOCUMENTS

| | | |
|---|---|---|
| DE | 3738090 A1 | 5/1989 |
| JP | 1066492 | 3/1989 |
| RU | 2074740 C1 | 3/1997 |
| WO | 9003157 | 4/1990 |
| WO | 0009061 | 2/2000 |
| WO | 0215837 | 2/2002 |
| WO | 2005056085 | 6/2005 |

OTHER PUBLICATIONS

Examination Report, GB0611219.7, Oct. 15, 2010, Intellectual Property Office, Great Britain, UK.

* cited by examiner

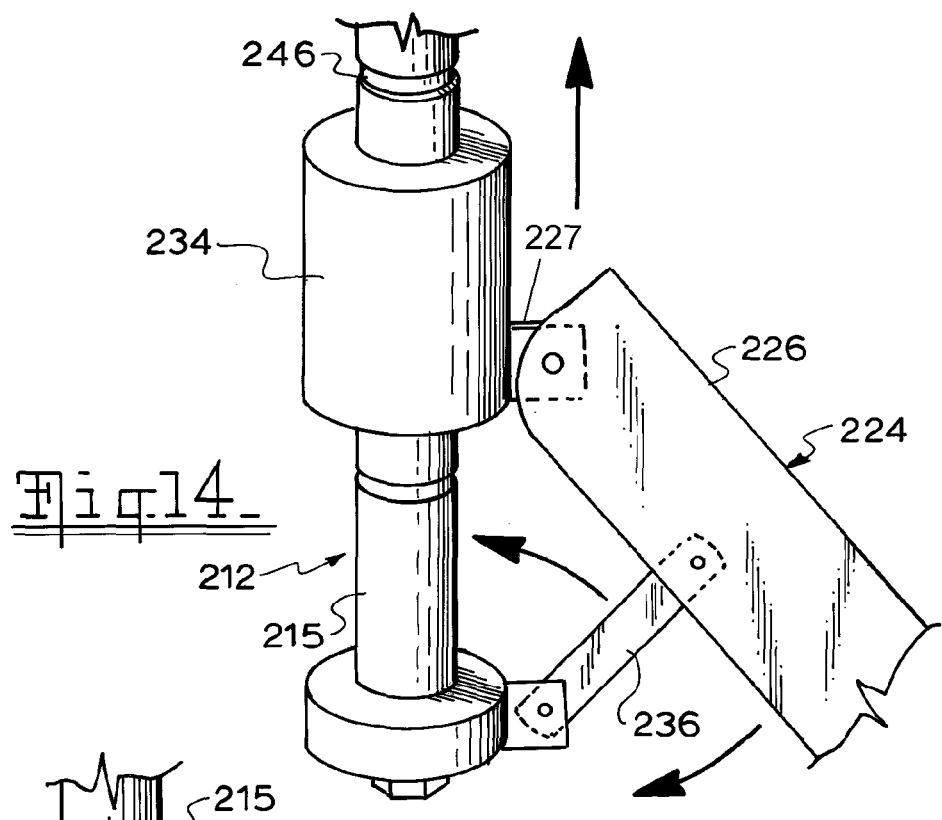
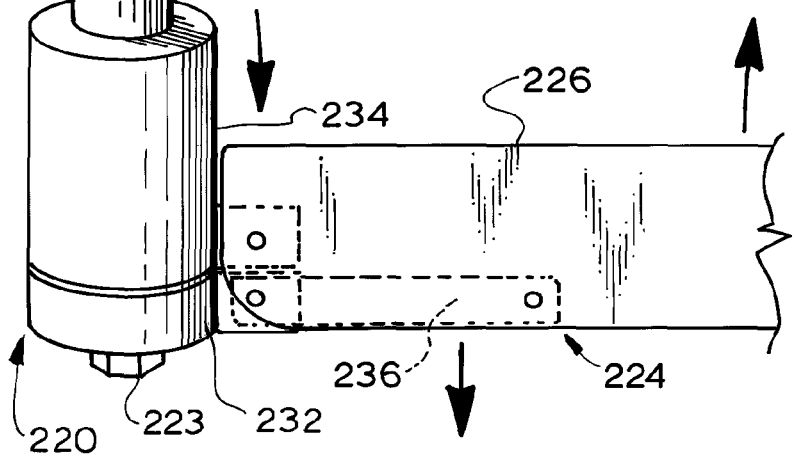
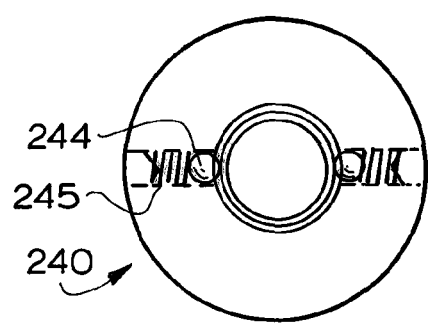
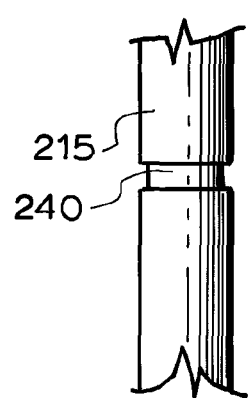

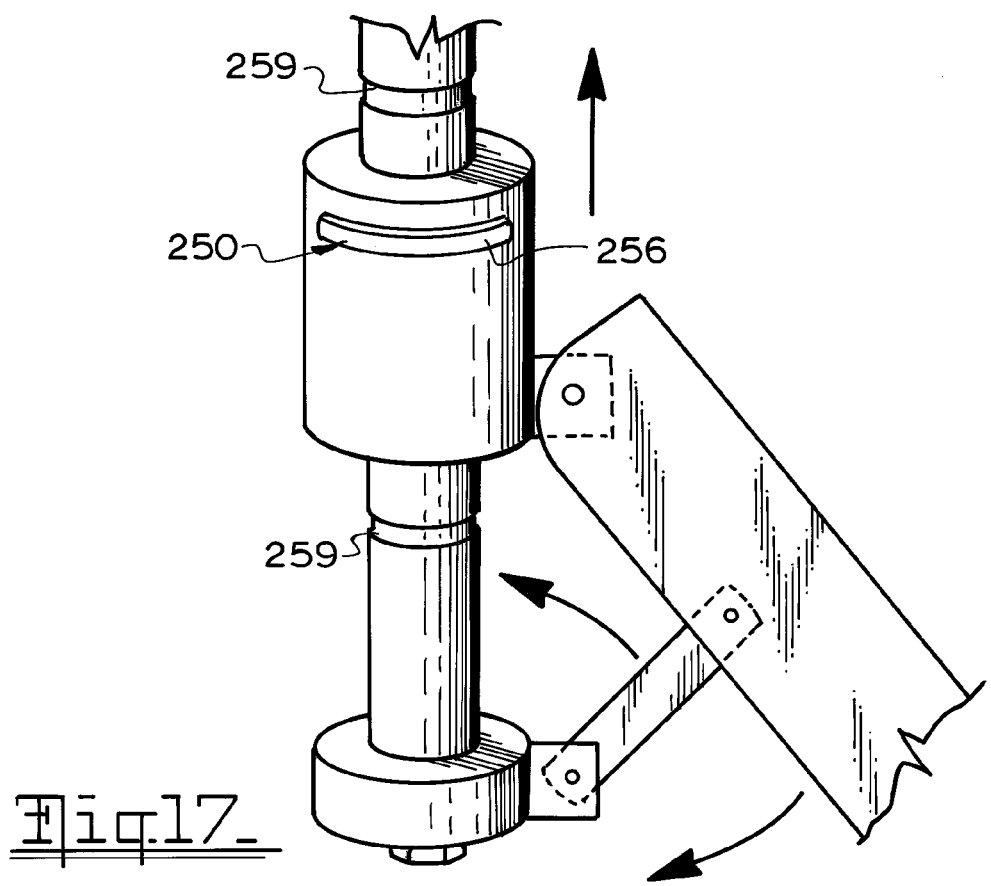
_Fig.17._
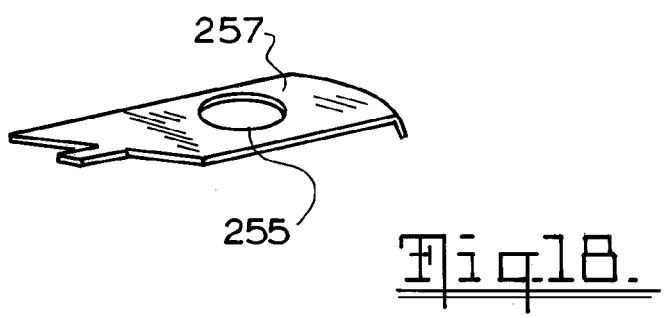
_Fig.18._
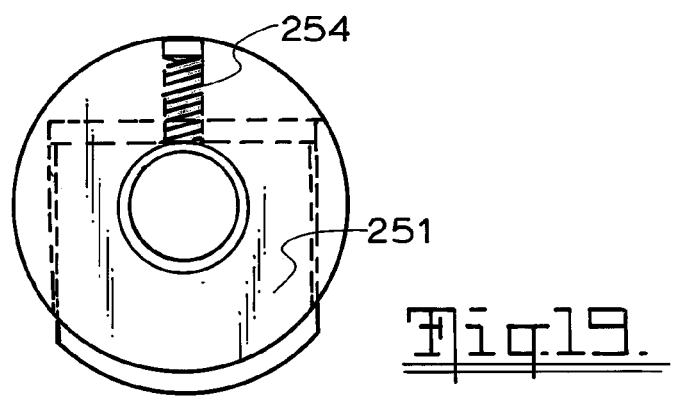
_Fig.19._

I.V. SUPPORT STAND AND CLAMP APPARATUS

The present application claims the priority of Australia Application No. 2005902977 filed on 8 Jun. 2005 and International Application PCT No. PCT/2004/001589, which claims priority to Australian Application No. 2003906942 filed 15 Dec. 2003 and Application No. 2004902625 filed 17 May 2004; all applications are hereby incorporated by reference.

FILED OF THE INVENTION

This invention relates generally to support stands and clamp apparatus and more particularly to I.V. support stands and apparatus.

BACKGROUND OF THE INVENTION

I.V. support stands are often used in hospitals and the like for supporting intravenous fluids containers or other equipment. Such support stands generally include an upright post and may have one or more arms at the upper end of the post to which bags or bottles containing intravenous fluids can be mounted. In some cases the post is used to support other equipment such as patient monitoring equipment, fluid pumps and the like. The post is in some cases carried on a base having ground engaging wheels. In other cases the post can be operatively connected to a support structure such as a trolley, bed, wheel chair or the like.

In one aspect of the present invention there is provided a support stand which provides inter alia versatility in operation.

Support stands according to some aspects of the invention may be adapted for use with the coupling assembly described in Australian Patent No. 753375 (200131436). The contents of Australian Patent No. 753375 (200131436) are incorporated herein by cross reference.

The present invention is concerned with an improvement to the apparatus previously described.

SUMMARY OF THE INVENTION

According to one aspect of the present invention there is provided a support stand including a support section for supporting articles or equipment thereon and a base, the base including a base body and a plurality of wheel assemblies, each wheel assembly including a wheel support operatively mounted to the base body for pivotal movement relative thereto and at least one wheel operatively mounted to the wheel support, the wheel supports being pivotally movable relative to the base body between an extended position in which the wheels rest on a support surface and retracted position, the arrangement being such that when the base is disposed on the support surface the wheels are caused to adopt the extended position and when the base is moved clear of the support surface the wheel assemblies are caused to adopt the retracted position. In the extended position the wheel support assemblies support the base and associated support stand on the support surface so that the support stand can travel over that surface.

In one form the base body includes a hub to which the support section of the support stand is mounted and a plurality of wheel support mountings are circumferentially disposed around the hub and extend therefrom, each support mounting being adapted to have mounted thereto one of the wheel supports.

In another form, the base body may include a plate member which is preferably circular when viewed in plan.

The support stand may include a pole which is operatively connected to the base body and in a preferred form is generally aligned with the central axis thereof. Mounting means which may be in the form of a boss operatively connected to the base body may be provided for mounting the pole to the base body.

The wheel supports may be in the form of leg members pivotally mounted to the base body and arranged so as to extend generally radially with respect to central axis thereof when in the extended position. In the retracted position the legs are more aligned with the central axis of the base body. In a preferred form, the leg members are inclined with respect to the central axis of the base body sufficiently to enable them to be able to adopt the extended position when moved from the retracted position to the extended position. Stop elements may be provided to limit the pivotal movement of the leg members to the inclined position. For example the stop elements may be defined by an end side of the leg members which is inclined to the side edges and abuts a section of the support mount when in the aligned position.

There may be further provided spring means associated with each wheel assembly for urging the supports into the retracted position. In another arrangement the supports are urged into the retracted position by gravity.

In another aspect, this invention resides in an apparatus for carrying articles including a support stand and a clamp assembly. The clamp assembly includes a clamp member adapted to be secured to a support structure which is adapted to be raised or lowered. The support stand includes a pole with a clamp mounting portion thereon and a base. The base includes a base body and a plurality of wheel assemblies, each wheel assembly including a wheel support operatively mounted to the base body for pivotal movement relative thereto and at least one wheel operatively mounted to the wheel support. The wheel supports are pivotally movable relative to the base body between an extended position and a retracted position so that the apparatus can adopt two modes of use including a first mode of use when the wheel supports are in the extended position the wheels can rest on a floor surface and the support stand is not held by the clamp member, and a second mode of use wherein the clamp mounting of the pole, is held by the clamp member and when the support structure is raised, the wheel supports can be moved into a retracted position in which the wheel supports are more closely aligned with a longitudinal axis of the pole than when in the extended position.

In a preferred embodiment the leg members when in the retracted position are inclined with respect to the central axis of the base body sufficiently to enable them to be able to adopt the extended position when moved from the retracted position to the extended position. The arrangement is such that when the wheels contact the floor surface when the wheel supports are in the retracted position, further movement of the support stand towards the floor surface causes the wheel supports to move into the extended position.

According to another aspect of the invention, there is provided a base for use with a support stand. The support stand includes a mounting member secured to a pole. The support stand may be of the type which can be held at a fixed holding station having stand mounting arms, each arm including a pin which is receivable within an aperture in the mounting member. The arrangement is such that when at the holding station the lower free end of the pole is spaced from the floor.

The base includes a main housing which may be in the form of a cylindrical body carried on a base wall. The housing may be closed at its upper end by an end plate. The base further includes a lifting mechanism comprising an elongated lifting member which may be in the form of a rod which is mounted for movement relative to the housing between extended and retracted positions. The lifting member has and upper end which includes a coupling member thereon which may be in the form of an elongated body of generally circular cross section having mounting apertures therein. The coupling member aperture is adapted to receive the lower end of the pole. A lock screw may be provided for retaining the end of the post within the aperture.

The base further includes an actuator assembly for causing movement of the lifting rod between the extended and retracted positions. The actuator assembly may include an actuating lever operatively connected to the rod via a connector link and operatively connected to the base by a second connector link. The lever may be in the form of a pedal which when depressed causes the lifting rod to move from the retracted position as shown to an extended position. The base may further include a damper for controlling return of the lifting rod to the retracted position.

In one preferred form the base according to this aspect of the invention may include wheel assemblies operatively mounted to the housing, the wheel assemblies being of the type described with reference to the first aspect of the invention in its broad or preferred forms.

According to yet another aspect of the present invention there is provided a support bracket suitable for use with a wheel chair, the wheel chair including a chair frame, the support bracket including a main body which in use is securable to the chain frame, the main body including first part and a second part which is movable relative to the first part between retracted position and an extended position, the second part including a mounting member to which a clamping element is adapted to be fitted.

In one form the first and second parts may be elongated members which are movable axially relative to one another between the retracted and extended positions. The first part may for example include a generally tubular body and the second part may be in the form of a rod telescopically receivable within the tubular body for movement between the extended and retracted positions.

Locking means may be provided to hold the two parts of the main body in the extended or retracted positions. The locking means may include a manually operable bolt having a threaded shank portion receivable within a complementary threaded boss on the first part of the main body. A knob may be provided at the end of the shank manual operation thereof causing the shank to move into or out of the interior of the tubular body.

The shank is adapted to be received within grooves on the second part to hold the two parts of the main body in position relative to one another.

The second part of the main body may further include a longitudinally extending groove therein which is adapted to receive the free end of the shank of the bolt so as to inhibit relative rotation between the two parts of the main body.

The mounting member may be in the form of a plate operatively connected to the free end of the second part of the main body. A pivotal coupling assembly may be provided between the mounting member and the second part of the main body to enable it to pivot relative thereto about one or more pivoted axes.

In a still further aspect this invention resides broadly in an apparatus for carrying articles including a support stand and a clamp assembly, the clamp assembly including a clamp member adapted to be secured to a support structure which is adapted to be raised or lowered, the support stand including, a post with a clamp mounting portion thereon and a base, the base including a base body and a plurality of wheel assemblies, each wheel assembly including a wheel support operatively mounted to the base body for pivotal movement relative thereto and at least one wheel operatively mounted to the wheel support, the wheel supports being pivotally movable relative to the base body between an extended position and a retracted position so that the apparatus can adopt two modes of use including a first mode of use when the wheel supports are in the extended position the wheels can rest on a floor surface and the support stand is not held by the clamp member, and a second mode of use wherein the clamp mounting of the post, is held by the clamp member and when the support structure is raised, the wheel supports can be moved into a retracted position in which the wheel supports are more closely aligned with a longitudinal axis of the post than when in the extended position wherein the base body includes a mounting hub to which the post is attached and an actuating member which is axially movable relative to the mounting hub, each wheel support being pivotally mounted to the actuating member and arranged that axial movement of the actuator causes movement of each support mounting between the extended and retracted positions.

Preferably the leg members when in the retracted position are inclined with respect to the central axis of the base body sufficiently to enable them to be able to adopt the extended position when moved from the retracted position to the extended position, the arrangement being such that when the wheels contact the floor surface when the wheel supports are in the retracted position further movement of the support stand towards the floor surface causes the wheel supports to move into the extended position.

There may be further provided a plurality of control links each associated with a respective wheel assembly and pivotally connected at one end to the mounting hub and at the other end to the wheel support. Each control link is configured so that when the wheel supports are in the extended position, they will tend to be maintained in that position even if the pole is raised clear of the floor surface. This may be achieved by providing an "over centre" connection where the link is connected to the mounting hub. When the leg members are in the extended position the connection of the link to the mounting hub is below the connection of the link to the leg member so the link is slightly inclined upwardly and outwardly. Furthermore, the weight of the actuating member may assist in holding the legs in the extended position. Thus the wheel supports can only be moved into the retracted position by movement of the actuator along the pole. A releasable locking assembly may be provided for releasably retaining the wheel supports at least in the retracted position.

In one form the releasable locking assembly includes a plurality of spring biased detents disposed within passages in the actuator which are adapted to cooperate with recess in the pole, the detents being biased in a direction so that they can locate within the recess to hold the actuator in that position. The arrangement is such that a force applied to the actuator will cause the detents to release from the recess.

In another arrangement the releasable locking assembly may include a spring biased locking plate in a passage within the actuator which has a locking edge receivable within a recess in the pole to hold the actuator in that position. Access to the plate may be via a slot in a wall of the actuator. The plate may be manually operated to move it from a holding position to a release position.

In a further embodiment, the releasable locking assembly may be adapted to automatically release from a holding position when weight is placed on the wheel supports, such as contacting the floor surface, to enable movement from the retracted position to the extended position without manual operation of the actuator.

BRIEF DESCRIPTION OF THE DRAWINGS

In order that this invention may be more readily understood and put into practical effect, reference will now be made to the accompanying drawings which illustrate preferred embodiments of the invention and wherein:

FIG. 14 is a partial schematic illustration of part of a support stand for use in apparatus according to the present invention;

FIG. 15 is a partial schematic illustration of the part of the support stand shown in FIG. 14 with the mounting arm in the extended position;

FIG. 16 is a schematic illustration of a releasable locking assembly which can form part of the support stand shown in FIGS. 14 and 15; and FIGS. 17 to 19 are schematic illustrations of a further embodiment of releasable locking assembly.

DETAILED DESCRIPTION OF PREFERRED EMBODIMENTS

Figure 1:
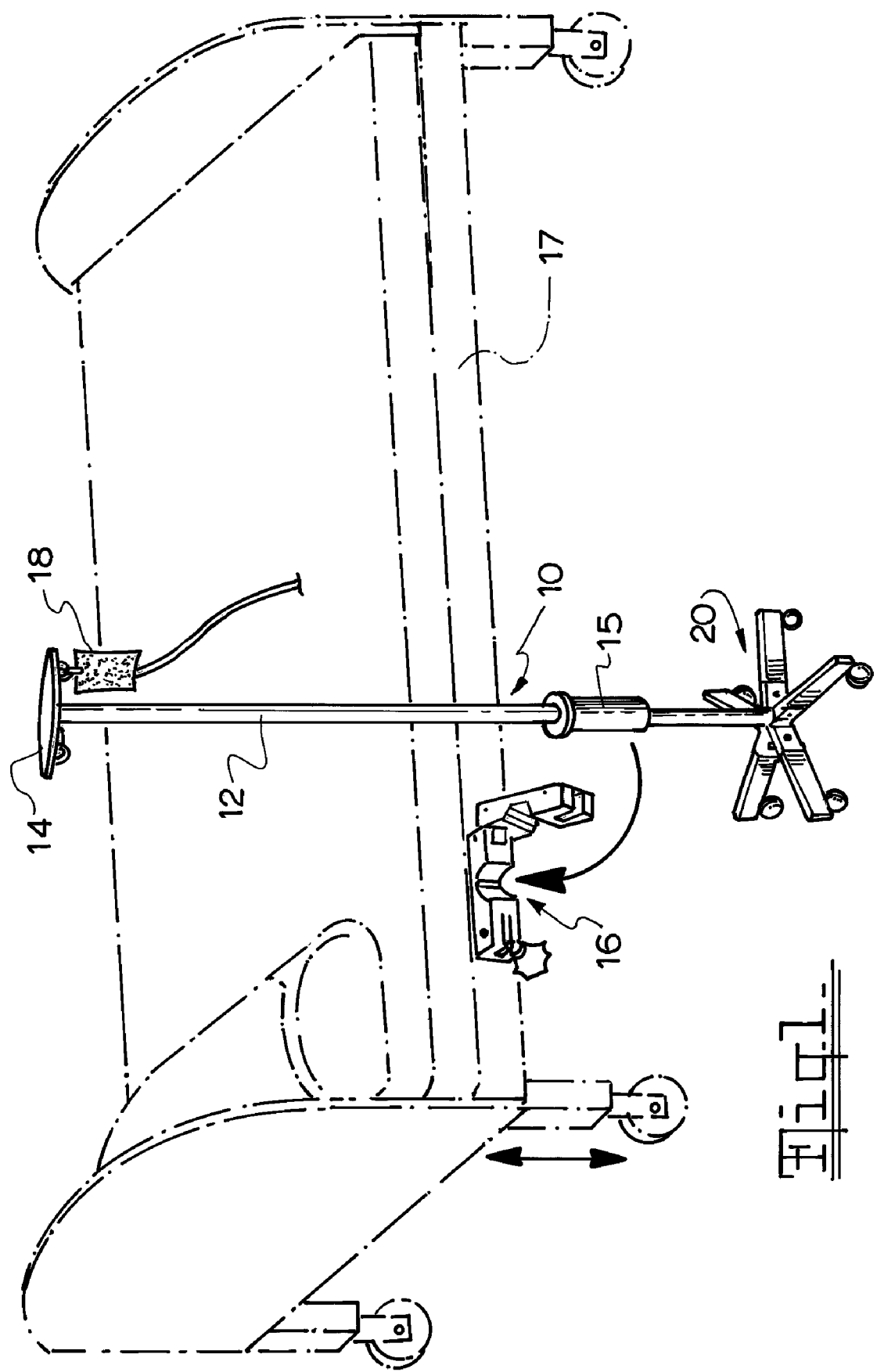
FIG. 1 is a schematic illustration of apparatus of the type to which the present invention relates.

Referring to FIG. 1, there is shown a support stand 10 which includes a pole 12 secured to a base 20, the pole 12 having at its upper end a support arm 14 to which intravenous fluid bags 18 or the like can be mounted. A sleeve 15 is fitted to the pole 12 at a selected position and is adapted to cooperate with clamping member 16 on bed frame 17. The clamping member 16 and cooperating sleeve 15 are, in essence, of the same configuration as the arrangement described in Australian Patent specification 753375 (200131436) except that the pole receiving aperture in the sleeve 15 extends all the way through the sleeve from one end to the other. The arrangement enables the support stand to be raised when the bed is raised in the same fashion described in the aforementioned patent specification.

Figure 2:
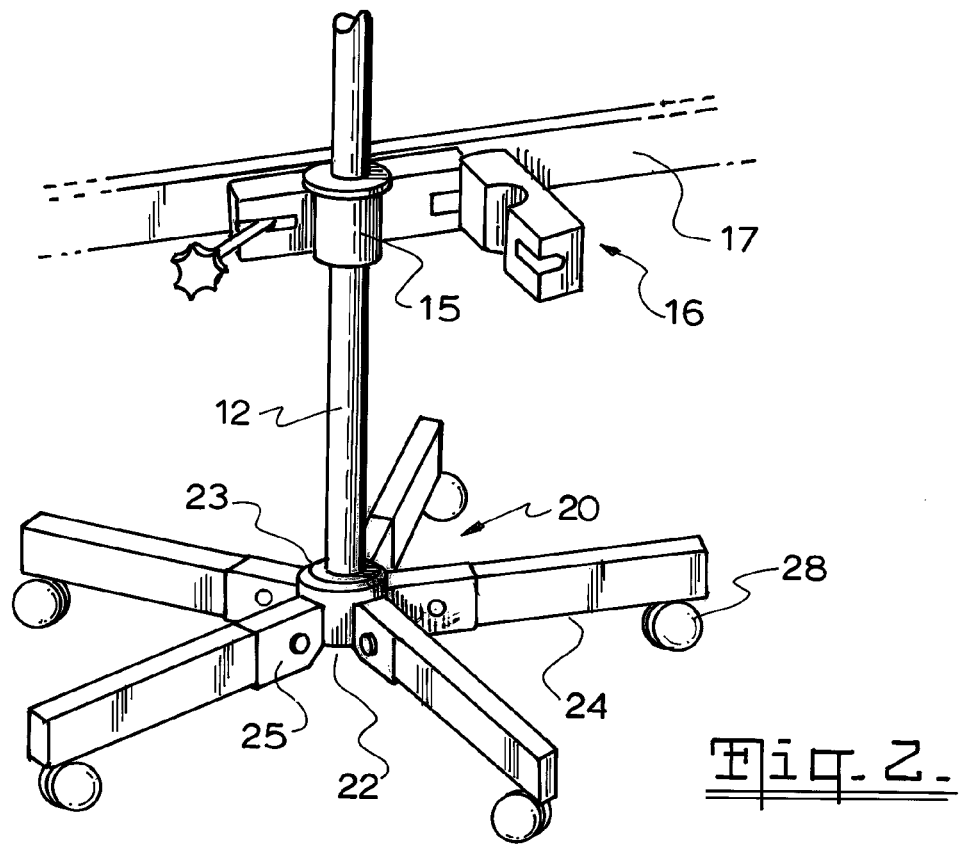
FIGS. 2 and 3 are schematic views of part of the support stand shown in FIG. 1 with the legs in the extended and retracted positions.
Figure 3:
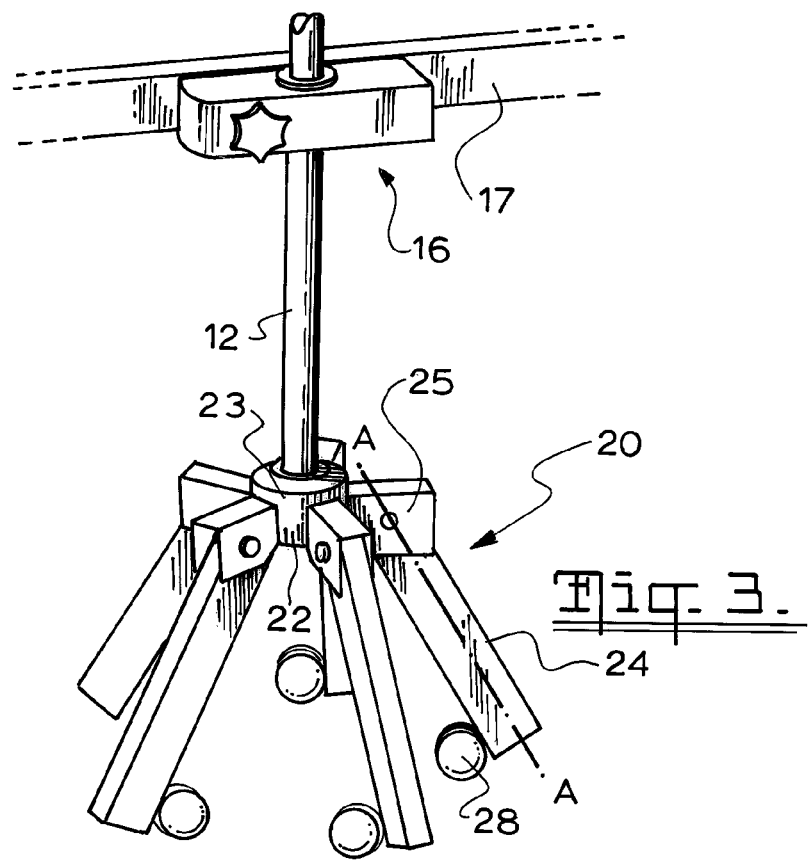
Figure 4:
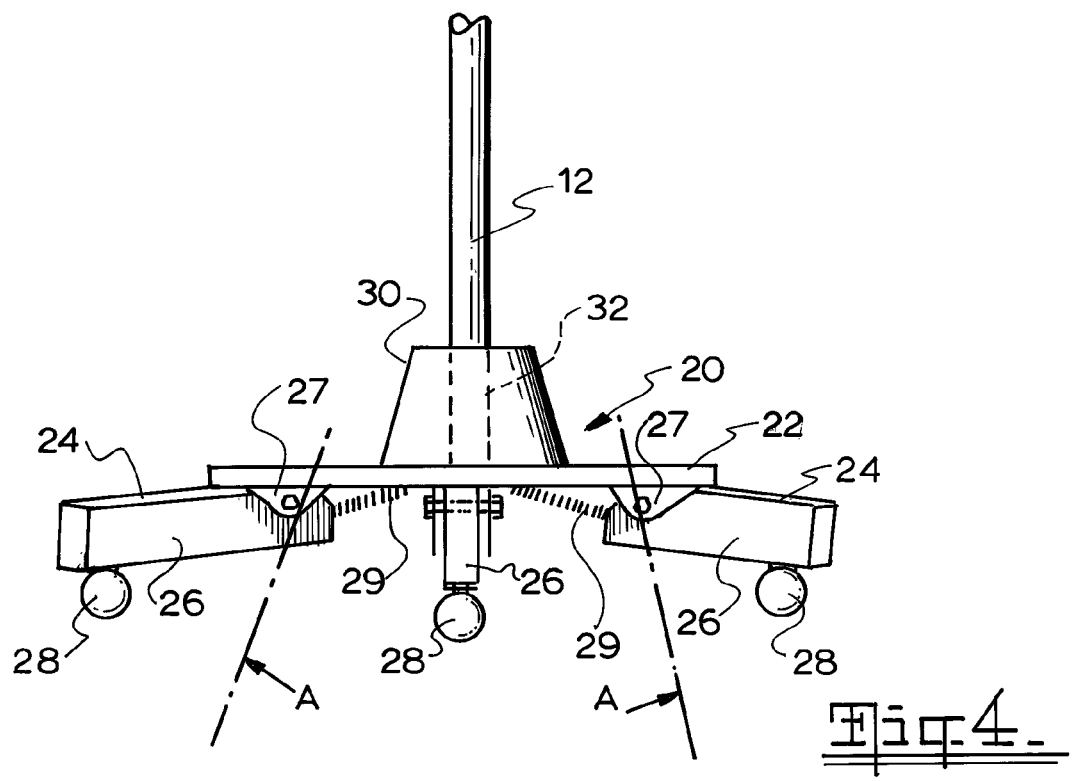
FIG. 4 is a schematic view of a modified form of support stand.

Referring in particular to FIGS. 2, 3 and 4, in this embodiment the base 20 includes a base body 22 which comprises a hub 23 to which the pole 12 is mounted at its lower end. The hub 23 has wheel support mounts 25 secured to its outer face the mounts 25 being circumferentially disposed around the boss and extending therefrom. Each wheel support mount 25 has associated therewith a wheel support assembly 24 including a wheel support 26 in the form of an elongated leg with a wheel 28 mounted thereto. The wheel 28 may be in the form of a castor or any other suitable type of ground engaging wheel.

As shown in FIG. 2, the stand 10 is resting on a floor or other support surface and the wheel supports 26 are in an extended position. As shown in FIG. 3, the stand 10 is raised above the floor (by raising the bed frame 17) and the wheel supports 26 may pivot under the influence of gravity to the position shown. When in the retracted position the axis A of each leg is inclined with respect to the pole 12 axis. This may be achieved by providing stops on each leg of the wheel support 26 to ensure that the leg can't pivot beyond the position shown. The stops may be defined by a part of the leg which abuts against the support mounts 25 to limit its movement. This ensures that when the stand 10 is lowered the supports will more easily track to the extended position.

Referring to FIG. 4, in this embodiment the base 20 includes a base body 22 and a plurality of wheel assemblies 24, each wheel assembly 24 including a wheel support 26 operatively mounted to the base body 22 for pivotal movement relative thereto. Each wheel support 26 has at least one wheel 28 operatively mounted thereon. The wheel supports 26 are pivotally mounted to the base body 22 via lugs 27 and movable between an extended position as shown in FIG. 4 in which the wheels rest on a support surface, such as a floor, and a retracted position. The retracted position is represented by the axes A in FIG. 4, the axes being the longitudinal axes of the wheel supports 26. The arrangement is such that when the base 20 is disposed on the support surface the wheels 28 are caused to adopt the extended position and when the base 20 is moved clear of the support surface the wheel assemblies 24 are caused to adopt the retracted position. In the extended position the wheel support assemblies 24 support the base 20 and associated support stand 10 on the support surface so that the support stand 10 can travel over that surface. The wheel supports 26 may be urged into the retracted position by means of springs 29.

The base 20 further includes a mounting boss 30 for mounting the pole 12 of the support stand 10 to the base 20. The boss 30 has an aperture 32 extending therethrough for receiving the lower end of the pole 12. The pole 12 is held in position by a bolt 33 and spring washer which extends through the base body 22 and is fastened to the pole 12.

When the support stand 10 is resting on the support surface, such as a floor, the wheel assemblies 24 of the base 20 are in the position shown in FIGS. 2 and FIG. 4; that is, the support stand 10 can travel over the floor with the wheels 28 in engagement with the floor. If it is required that the support stand 10 be connected to a bed mostly likely by the bed frame 17, the sleeve 15 is disposed within clamping member 16 which is locked and the bed raised so that the base 20 is clear of the floor. In this position, the wheel assemblies 24 will adopt the retracted position and the bed and stand 10 can be moved without the wheel assemblies 24 of the base 20 causing undue interference; that is when the base is clear of the support surface the wheel supports 26 are urged into the retracted position. As is indicated in FIG. 3, the wheel support/s 26 are inclined outwardly from the inner end towards the outer end when in the retracted position. This enables the wheel assemblies 24 to return to the extended position when the stand 10 is lowered to the floor.

Figure 5:
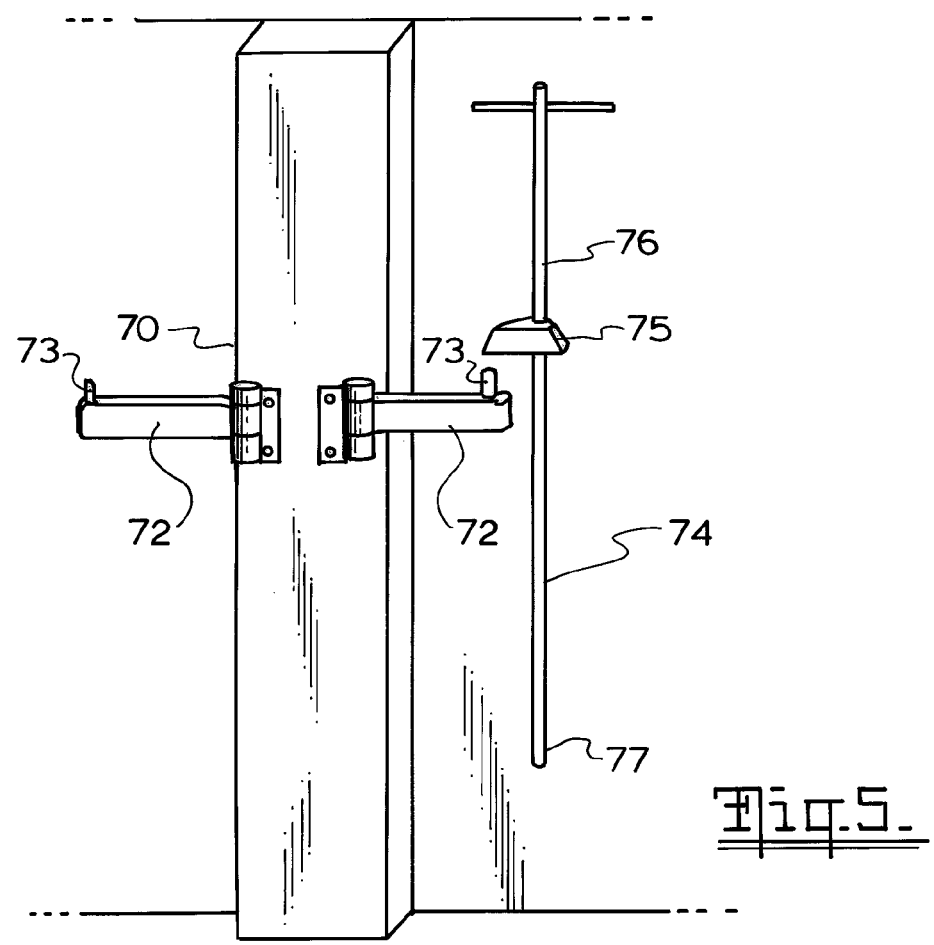
FIG. 5 is an illustration of a further embodiment employing a system an arrangement for handling support stands.
Figure 6:
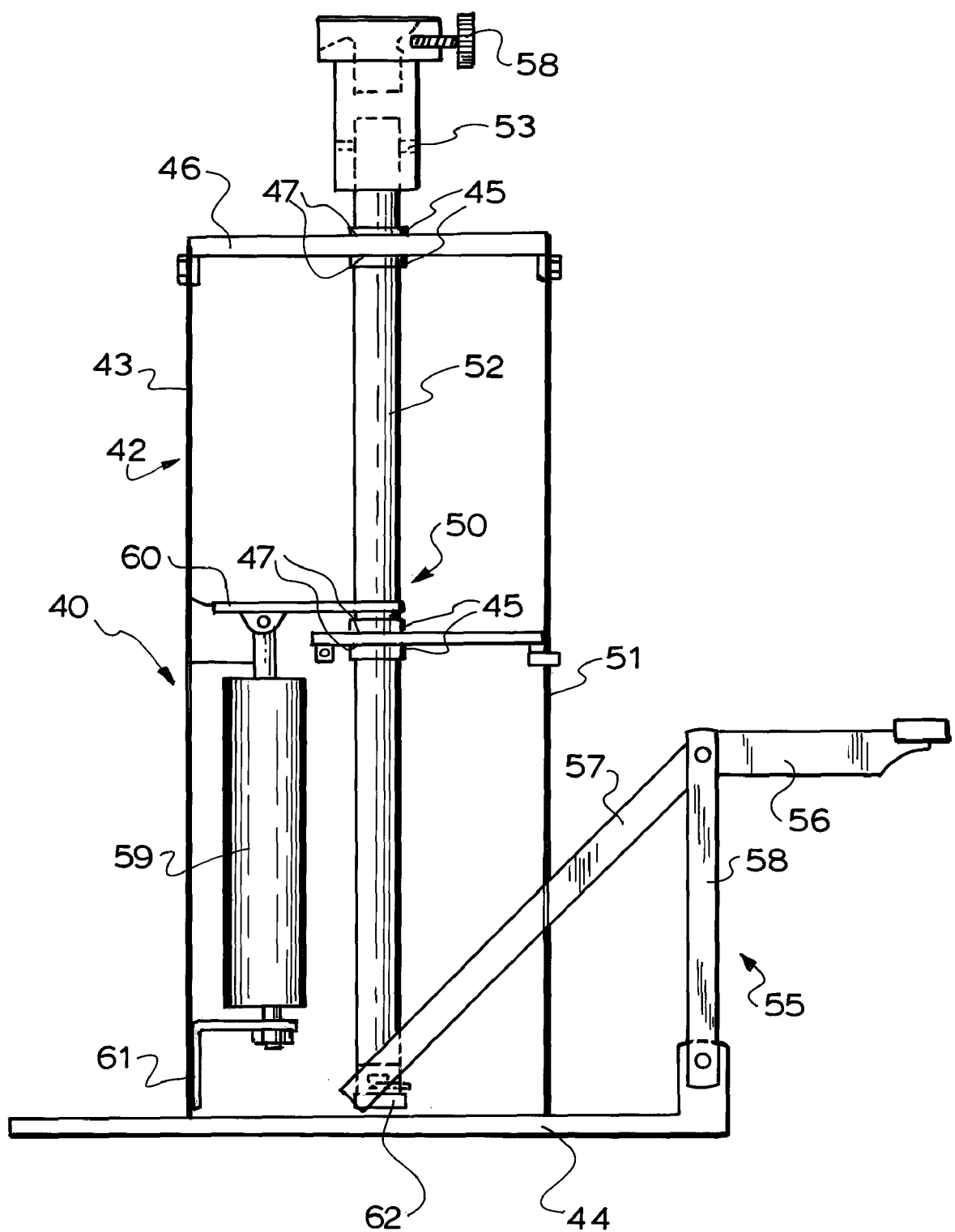
FIG. 6 is a schematic side elevation cross section of a base for use with support stands of the type shown in FIG. 5.
Figures 7, 8:
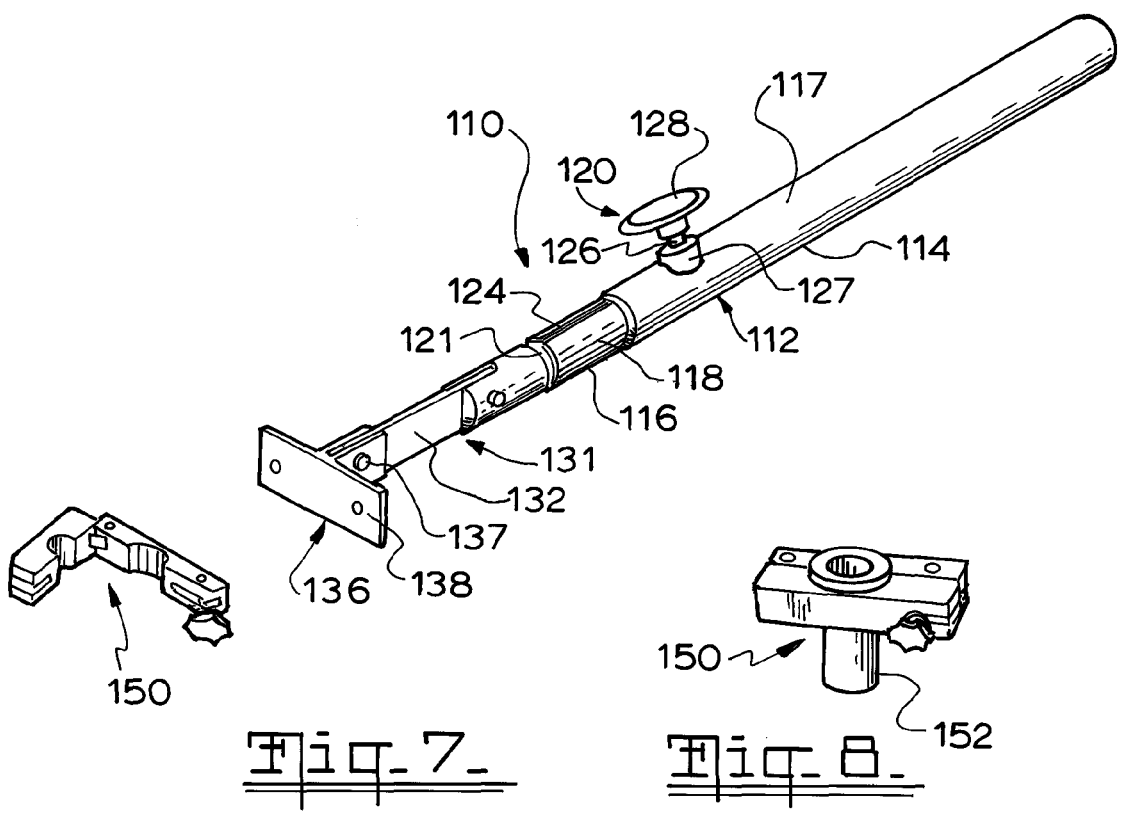
FIG. 7 is a schematic isometric view of a support bracket according to another embodiment.
FIG. 8 is a schematic view of a clamp for an IV pole for use with the support bracket.
Figure 9:
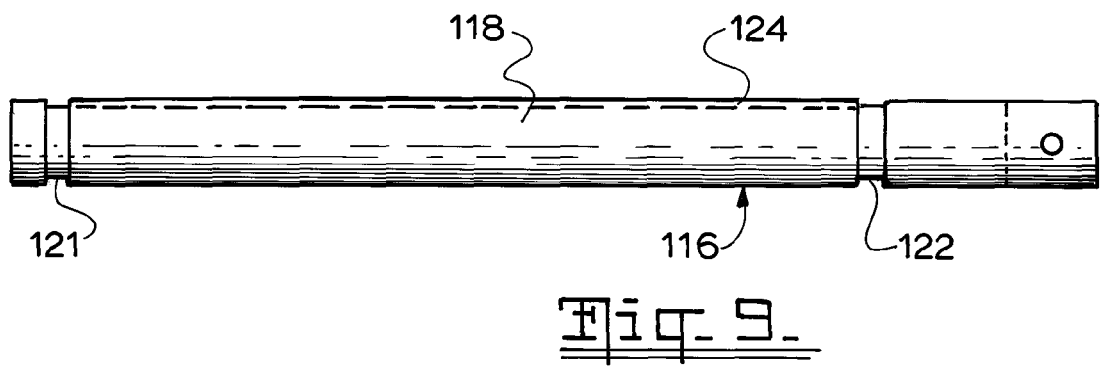
FIG. 9 is a side elevation of part of the main body of the support bracket shown in FIG. 7.
Figure 10:
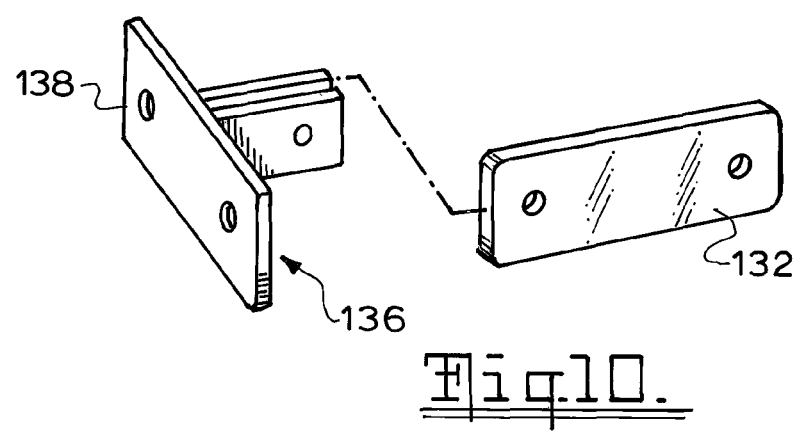
FIG. 10 is a schematic view of the mounting member and coupling member shown in FIG. 7.
Figure 11:
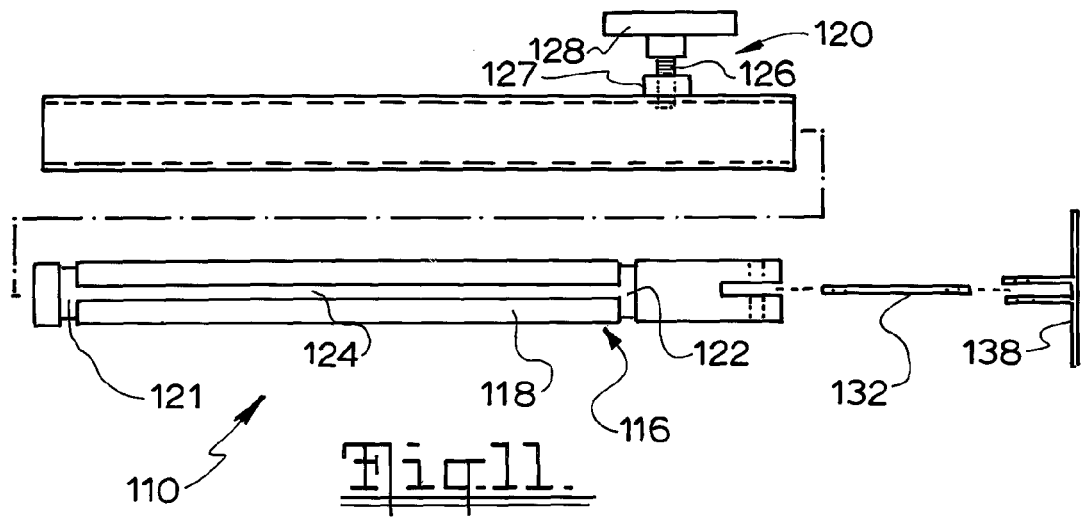
FIG. 11 is an exploded side elevation of the support bracket shown in FIG. 7.

Referring to FIG. 6 there is shown the base 40 for a support stand which is of the type shown in FIG. 5 or other types of pedant IV poles. As shown in FIG. 5 the support stand 74 may include intravenous bags and the like thereon. A mounting member 75 is secured to the pole 72. The support stand 74 is of the type which can be held at a fixed holding station 70 having stand mounting arms 72, each arm including a pin 73 which is receivable within an aperture in the mounting member 75. It will be appreciated that a number of support stands 74 can be held at the station 70. A person skilled in the art would also be able to understand that other mounting systems of the support stand 75 to the holding station 70 are just as applicable as the pin 73 and matching aperture arrangement. As can be seen in FIG. 5, when at the holding station 70 the lower free end 77 of the pole is spaced from the floor.

As shown in the embodiment of FIG. 6, the base 40 may include a main housing 42 comprising a cylindrical body 43 carried on a base wall 44. The housing 42 is closed at its upper end by end plate 46. The base 40 may further include a lifting mechanism 50 comprising an elongated lifting member 52 in the form of a rod which is mounted for movement relative to the housing 42 between extended and retracted positions. The rod 52 passes through bronze bushes 45 held by circlips 47. The upper end of the lifting rod 52 includes a coupling member 53 thereon which is an elongated body of generally circular cross section having mounting apertures therein. The upper mounting aperture is adapted to receive the lower end 66 of the pole 60. A lock screw 58 provides for retaining the end of the post within the aperture. Locking pins (not shown) hold the coupling member 53 on the lifting rod 52.

The base 40 further includes an actuator assembly 55 for causing movement of the lifting rod 52 between the extended and retracted positions. The actuator assembly 55 includes an actuating lever 56 operatively connected to the rod 52 via a connector link 57 which passes through a slot 51 in the housing 42 and operatively connected to the base 40 by a second connector link 58. An end plug 62 is provided in the end of the rod 52 to which the link 57 is pivotally connected. The lever 56 is in the form of a pedal which when depressed causes the lifting rod 52 to move from the retracted position, as shown, to an extended position. The base 40 further includes a damper 59 for controlling return of the lifting rod 52 to the retracted position, the damper rod 59 being connected to the rod 52 via plate 60. The damper 59 is mounted to bracket 61 on the housing.

In one preferred form the base wall 44 may have operatively mounted thereon wheel assemblies 24 of the type described with reference to FIGS. 2 to 4. The base 40 is suitable for safely lifting and moving pendant IV poles such as illustrated in FIG. 5 and can be used with a clamping member 16 attached to a bed frame or a wheel chair.

Referring to the FIGS. 7 to 13 of the drawings there is shown a support bracket generally indicated at 110. The support bracket 110 is adapted to be mounted to a structure which in one preferred application may be the frame of a wheel chair or the like. The support bracket 110 is adapted to have fitted to a clamp 150 which can releasably carry the pole 12 or pole mount 15 of an IV stand or the like (see FIG. 5).

The support bracket 110 includes a main body 112 which is mounted to the frame of a wheel chair for example. The main body 112 includes two elongated first and second parts 114 and 116 each having a longitudinal axis, which axes are co-axially aligned or generally parallel to one another. The two parts 114 and 116 are movable relative to one another in the direction of the longitudinal axes between an extended and a retracted position.

The first part 114 is in the form of an elongated tube 117 which can be attached to the frame of the wheel chair. The second part 116 is in the form of a rod 118 telescopically receivable within the tube 117 and slidable relative thereto between the extended and retracted positions. The rod 118 includes two circumferential grooves 121 and 122 therein and a longitudinally extending slot 124. A locking pin 120 having a threaded shank 126 disposed within a complementary threaded boss 127 on the tube 117 is operable by knob 128 to hold the tube 117 and rod 118 in fixed position relative to one another. When the shank 126 is within groove 124 relative rotation between the tube and rod is inhibited. The circumferential grooves 121 and 122 limit the relative longitudinal movement between the tube 117 and rod 118 between the extended and retracted positions.

At the free end of the rod 118 a mounting assembly 131 is provided which includes a connecting plate 132 which is pivotally connected thereto for allowing movement about the axis of pivot bolt or other fastener 133. A locking device (not shown) may be provided for locking connecting plate 132 to the second part 116. A mounting member 136 is operatively connected to connecting plate 132 for pivotal movement about pivot bolt or other type of fastener 137. The mounting member 136 is in the form of a plate 138 to which a clamp 150 of the type for example in Australian Patent 753375 (200131436) can be fitted.

Operation of the support bracket 110 will hereinafter be described. The bracket 110 is mounted for example to the frame of a wheel chair and positioned so that the tube 117 does not protrude from the wheel chair frame. When the support bracket 110 is not required for use the tube 117 and rod 118 are in the fully retracted position. When the bracket 110 is required for use it is moved to the extended position so that the tube 117 extends away from the wheel chair frame. The mounting plate 131 may have a clamp 150 already attached thereto or may have a clamp 150 attached at this time ready to receive the IV pole. Pivot bolts are set so that the plate 131 is at the required orientation.

Figure 12:
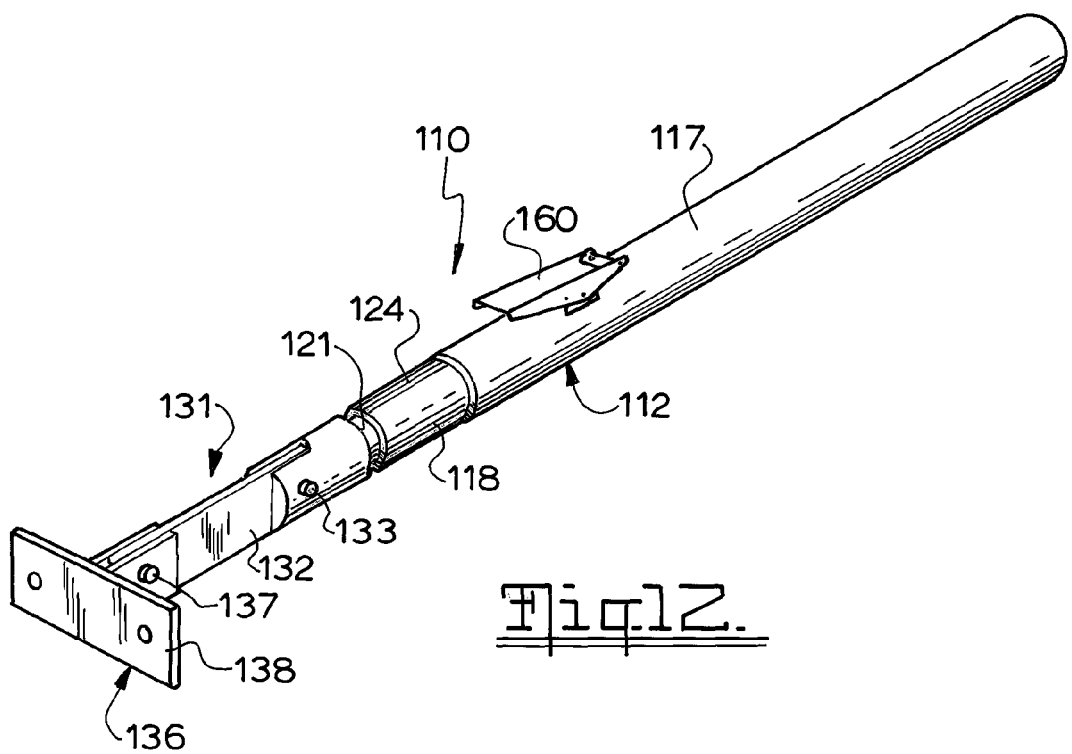
FIG. 12 is a schematic isometric view of another form of support bracket.
Figure 13:
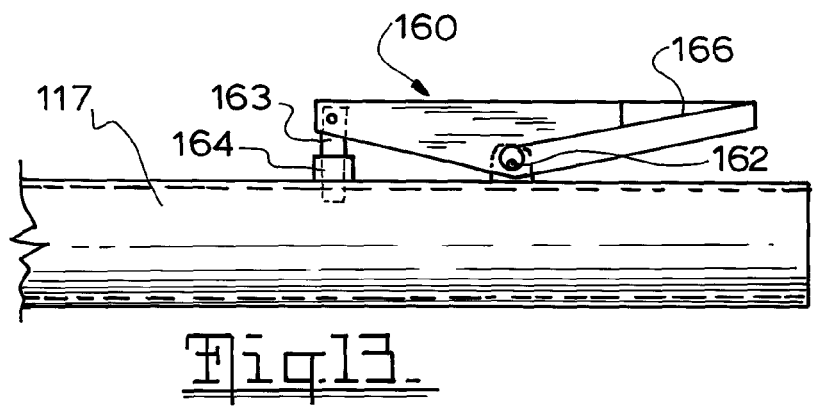
FIG. 13 is a schematic detail of part of the bracket shown in FIG. 12.

The support bracket 110 as shown in FIGS. 12 and 13 is substantially the same as that shown in FIGS. 7-11 except that the locking pin 120 has been replaced by a locking lever 160. The locking lever 160 is pivotally mounted to tube 117 via pivot mounting 162. A locking pin 163 is operatively connected to the lever and passes through a boss 164 on the tube so that the pin 163 can enter the grooves on the rod 118. A return spring 166 urges the lever into the position shown in FIG. 13.

In a preferred embodiment, the support bracket 110 and clamp 150 are utilised on a wheel chair to enable convenient movement of a patient and an IV stand by a single person.

Referring to FIGS. 14 to 19 there is shown a part of a support stand for use in apparatus according to the present invention. The support stand 212 is for apparatus of the type shown in FIG. 1. The support stand 212 includes a pole 215 to which intravenous fluid bags and/or other medical and auxiliary equipment can be mounted. The support stand 212 includes a mounting portion such as sleeve 15 in FIG. 1 which is adapted to cooperate with a clamping member 16 on a bed frame 17, the bed frame being adapted to be raised or lowered. FIGS. 14 to 19 do not illustrate this part of the support stand.

As with the earlier described arrangement the support stand 212 includes a base 220 including a mounting hub 232 to which pole 215 is attached via a nut and bolt assembly 223. The base 220 further includes an actuator 234 in the form of a sleeve which is axially slidable along the pole 215.

The apparatus further includes a plurality of wheel assemblies 224. Only one is shown in FIGS. 14 and 15 but at least three are provided as described in the earlier embodiments. Each wheel assembly 224 includes a wheel support 226 in the form of a leg member to which a wheel (not shown) is mounted. As shown, each wheel support 226 is pivotally mounted to the actuator 234 at pivot mounting 227. Each wheel support 226 also has a control link 236 associated therewith, each control link 236 being pivotally mounted at one end to the mounting hub 232 and at the other end pivotally mounted to the wheel support 226 with which it is associated.

It will be apparent that by manual operation of the actuator it can be moved along the pole 215 so as the cause the wheel support 226 to move between the extended position as shown in FIG. 15 to a retracted position. In FIG. 14 the wheel supports 236 are between the extended and retracted positions. In this particular embodiment, the control links 236 are configured so that when the wheel supports 226 are in the extended position, they will tend to be maintained in that position even if the pole 215 is raised clear of the floor surface. Thus the wheel supports 226 can only be moved into the retracted position by movement of the actuator 234 along the pole as shown in FIG. 14.

One form of releasable locking assembly 240 is shown in FIG. 16 which assists in holding the wheel supports 226 in the retracted position. The locking assembly 240 includes a plurality of detents 244 disposed within passages in the actuator 234, the detents 244 being biased inwardly by springs 245. The detents 244 are adapted to cooperate with a recess 246 in the pole 115 so that they can locate therein to hold the actuator 234 in that position in the pole. The arrangement is such that a force applied to the actuator 234 will cause the detents 244 to release from the recess.

Another form of locking assembly 250 is shown in FIGS. 17 to 19. In this form the assembly includes a locking plate 251 receivable within a passage in the actuator 234. The plate 251 includes a locking tongue 255 which is receivable within slots 259 in the pole. A spring 254 urges the plate 251 towards the recess. Access to the plate 251 for operation is via slot 256.

The wheel supports 226 are preferably arranged so that when in the retracted position they are inclined with respect to the central axis of the base body sufficiently to enable them to be able to adopt the extended position when moved from the retracted position to the extended position. The arrangement is such that when the wheels contact the floor surface when the wheel supports 226 are in the retracted position, further movement of the support stand towards the floor surface causes the wheel supports 226 to move into the extended position.

In a preferred embodiment the actuator 234 is manually operated to move the wheel supports 226 into a retractor position. This is a convenient position for moving an IV stand which may be clamped to a bed. Once the bed and IV stand have been transported and as the bed is lowered weight is placed onto the wheel supports 226 when they contact the floor causing the wheel supports 226 to automatically extend without manual operation of the actuator 234.

It is to be understood that the inventive concept in any of its aspects can be incorporated in many different constructions so that the generality of the preceding description is not to be superseded by the particularity of the attached drawings. Various alterations, modifications and/or additions may be incorporated into the various constructions and arrangements of parts without departing from the spirit or ambit of the invention.

The invention claimed is:

1. An apparatus for carrying articles including a support stand and a clamp assembly, the clamp assembly including a clamp member adapted to be secured to a support structure which is adapted to be raised or lowered, the support stand including a pole having a longitudinal axis with a clamp mounting portion thereon and a mounting hub to which the pole is attached, an actuating member which is axially movable relative to the mounting hub along the pole above said mounting hub, a plurality of wheel assemblies each including a wheel support pivotally mounted at an inner end to the actuating member and at least one wheel operatively mounted to an outer end of the wheel support, and a control link wherein one end of the control link is pivotally connected intermediate said inner and outer ends of the wheel support and the opposite end of the control link is pivotally connected to the mounting hub, whereby axial movement of the actuating member away from said mounting hub follows movement of each wheel support between a position extending substantially radially of the actuating member where the wheels rest on a floor surface when the clamp member is released, and a retracted position where the pole is held by the clamp member and in which the wheel supports lay substantially adjacent the pole and mounting hub, the wheel supports when in the retracted position being inclined with respect to the longitudinal axis of the pole and mounting hub whereby when the wheels contact a floor surface when the wheel supports are in the retracted position, further movement of the support stand toward the floor surface causes the wheel supports to move into the extended position.

2. The apparatus according to claim 1, wherein the mounting hub includes a plurality of wheel support mountings circumferentially spaced about the mounting hub and extending therefrom, each support mounting being adapted to have pivotally mounted thereto one of the wheel supports.

3. The apparatus according to claim 1, wherein the wheel supports are biased to the retracted position by the influence of gravity on said wheel supports.

4. The apparatus according to claim 1, including a releasable locking assembly for releasably retaining the wheel supports in the retracted position.

5. The apparatus according to claim 4, wherein the releasable locking assembly includes a spring loaded ball-and-detent arrangement between the pole and the actuating member.

6. The apparatus according to claim 1, wherein each control link is configured to provide a limit of movement of said wheel supports at an extended position.

7. The apparatus according to claim 4, wherein the releasable locking assembly is adapted to automatically release from a holding position when load is placed on the pole to enable movement of the wheel supports from the retracted position to the extended position without manual operation of the actuator.

8. The apparatus according to claim 5, wherein there is provided a second detent recess adapted to engage said detent ball when said wheel supports are in their extended position.

9. The apparatus according to claim 1, wherein a limit of deployment of said wheel supports is provided by said actuating member contacting said mounting hub.

* * * * *